(12) United States Patent
Miller et al.

(10) Patent No.: US 8,588,879 B2
(45) Date of Patent: Nov. 19, 2013

(54) MOTION COMPENSATION IN A SENSOR

(71) Applicant: Covidien LP, Mansfield, MA (US)

(72) Inventors: Mark C. Miller, Longmont, CO (US); Charles Haisley, Boulder, CO (US); Jill Klomhaus Anderson, Longmont, CO (US); Edward M. McKenna, Boulder, CO (US); Braddon M. Van Slyke, Arvada, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/841,157

(22) Filed: Mar. 15, 2013

(65) Prior Publication Data

US 2013/0217988 A1   Aug. 22, 2013

Related U.S. Application Data

(63) Continuation of application No. 12/714,531, filed on Feb. 28, 2010, now Pat. No. 8,483,788.

(51) Int. Cl.
*A61B 5/00* (2006.01)

(52) U.S. Cl.
USPC ............................................. 600/323

(58) Field of Classification Search
USPC ............................................. 600/323
See application file for complete search history.

(56) References Cited

U.S. PATENT DOCUMENTS

| | | | |
|---|---|---|---|
| 5,025,791 A * | 6/1991 | Niwa | 600/483 |
| 5,645,060 A | 7/1997 | Yorkey | |
| 5,964,701 A | 10/1999 | Asada et al. | |
| 6,018,673 A | 1/2000 | Chin et al. | |
| 6,434,408 B1 | 8/2002 | Heckel | |
| 6,839,582 B2 | 1/2005 | Heckel | |
| 6,845,256 B2 | 1/2005 | Chin et al. | |
| 6,879,850 B2 | 4/2005 | Kimball | |
| 7,260,425 B2 | 8/2007 | Chin et al. | |
| 8,073,518 B2 | 12/2011 | Chin et al. | |
| 8,460,189 B2 * | 6/2013 | Libbus et al. | 600/301 |
| 2002/0103423 A1 | 8/2002 | Chin et al. | |
| 2004/0034293 A1 | 2/2004 | Kimball | |
| 2007/0208233 A1 * | 9/2007 | Kovacs | 600/300 |
| 2007/0299328 A1 | 12/2007 | Chin et al. | |
| 2008/0081973 A1 | 4/2008 | Hoarau | |

* cited by examiner

*Primary Examiner* — Clayton E Laballe
*Assistant Examiner* — Linda B Smith
(74) *Attorney, Agent, or Firm* — Fletcher Yoder PC

(57) ABSTRACT

A physiological sensor includes an emitter configured to transmit light and a detector configured to receive the transmitted light. The sensor also includes a first accelerometer disposed on a first portion of the sensor and a second accelerometer disposed on a second portion of the sensor, the second portion opposing the first portion. The first and second accelerometers are configured to measure a change in motion that corresponds to a change in distance between the detector and the emitter.

19 Claims, 4 Drawing Sheets

MOTION COMPENSATION IN A SENSOR

CROSS-REFERENCE TO RELATED APPLICATIONS

This application is a continuation of U.S. application Ser. No. 12/714,531, filed Feb. 28, 2010, entitled "Motion Compensation in a Sensor," the disclosure of which is hereby incorporated by reference in its entirety.

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

The light sources utilized in pulse oximeters typically are placed in a certain position on a patient. For the sensor to operate optimally, this position should be maintained. Accordingly, movement of the sensor due to the movements of a patient may lead to erroneous results.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to non-invasively measuring physiologic parameters corresponding to blood flow in a patient by emitting light into a patient's tissue with light emitters (e.g., light emitting diodes) and photoelectrically detecting the light after it has passed through the patient's tissue. More specifically, present embodiments are directed to a pulse oximeter that includes a sensor and a monitor. The sensor may include at least one accelerometer that may operate to measure a change in distance between the emitter and the detector of the sensor. The sensor may transmit the measured change in the distance between the emitter and the detector to a motion processor in a pulse oximetry monitor. The motion processor may calculate an gain factor corresponding to the change in the distance between the detector and the emitter via, for example, an equation related to a model distance between the emitter and the detector, an expectation model of photon behavior between the emitter and the detector, and the measurements from the accelerometer. Alternatively, the motion processor may calculate an attenuation factor corresponding to the change in the distance between the detector and the emitter via, for example, comparing the measurements received from the one or more accelerometers with motion measurements and corresponding attenuation factors stored in a look-up table (e.g., stored in a table memory). The calculated attenuation factor may be used by the monitor to compensate for movement in a sensor when calculating physiological parameters of a patient.

Figure 1:
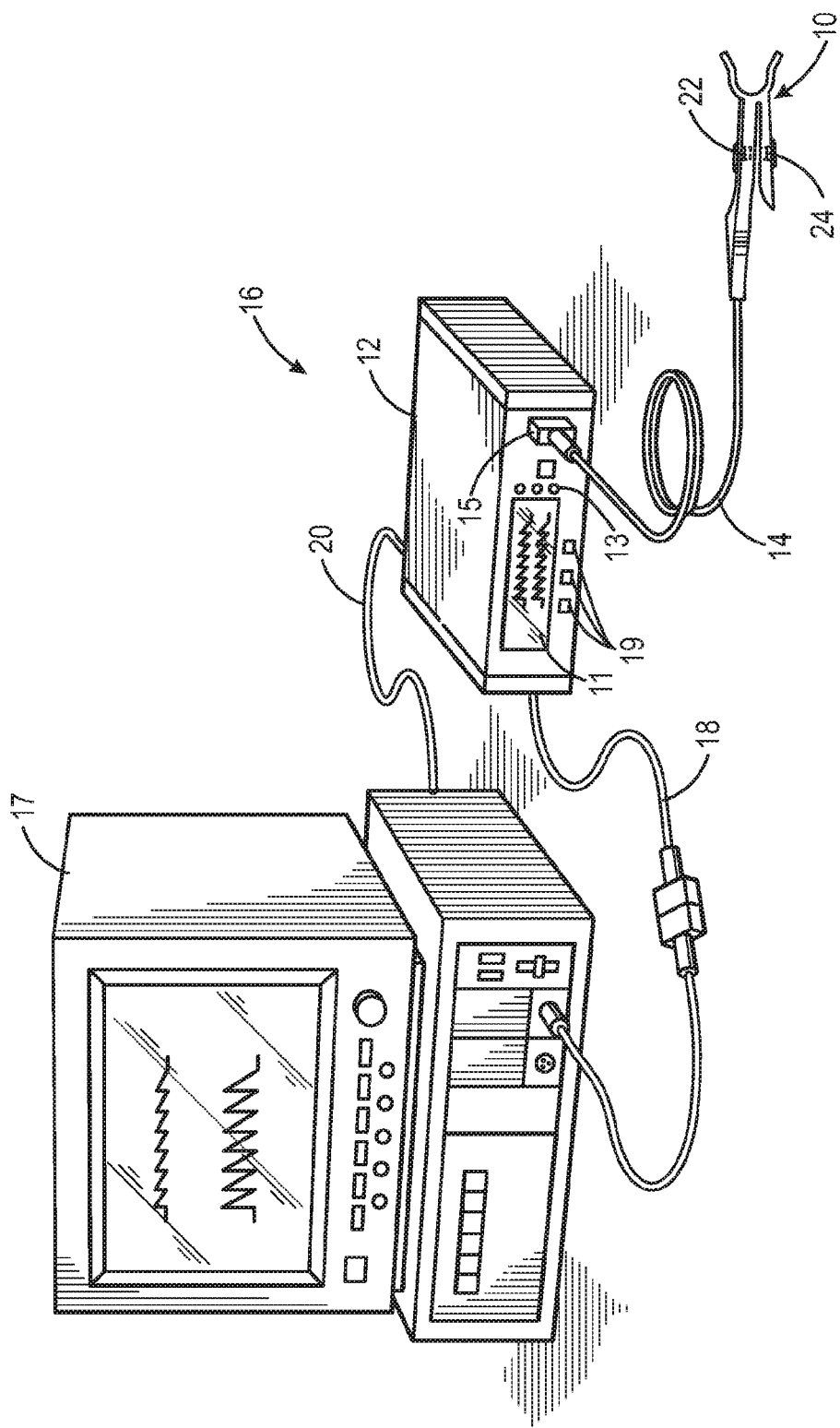
FIG. 1 illustrates a perspective view of a pulse oximeter in accordance with an embodiment.

FIG. 1 depicts a sensor 10 that may be used in conjunction with a monitor 12 in accordance with an embodiment of the present disclosure. The sensor 10 may be coupled to the monitor 12 via sensor cable 14 and sensor connector 15, or the sensor 10 may be coupled to a transmission device (not shown) to facilitate wireless transmission between the sensor 10 and the monitor 12. It should be noted that sensor cable 14 may be able to transmit a plurality of signals to the sensor 10 as well as transmit a plurality of signals from the sensor 10 to the monitor 12. The sensor 10 and the monitor 12 may generally be referred to as a pulse oximeter 16. Pulse oximeter 16 may be any suitable pulse oximeter, such as those available from Nellcor Puritan Bennett, LLC.

The monitor 12 of the pulse oximeter 16 may be configured to display calculated parameters on a display 11. As illustrated in FIG. 1, the display 11 may be integrated into the monitor 12 and may be configured to display computed physiological data including, for example, an oxygen saturation percentage, a pulse rate, and/or a plethysmographic waveform of a patient. As is known in the art, the oxygen saturation percentage may be a functional arterial hemoglobin oxygen saturation measurement in units of percentage $SpO_2$, while the pulse rate may indicate a patient's pulse rate in beats per minute. The monitor 12 may also display information related to alarms, monitor settings, and/or signal quality via indicator lights 13.

Furthermore, to upgrade conventional operation provided by the monitor 12 (e.g., to provide additional functions), the monitor 12 may be coupled to a multi-parameter patient monitor 17 via a cable 18 connected to a sensor input port or via a cable 20 connected to a digital communication port, or through wireless transmission components (not shown). To facilitate user input, the monitor 12 may include a plurality of control inputs 19. The control inputs 19 may include fixed function keys, programmable function keys, and soft keys. Specifically, the control inputs 19 may correspond to soft key icons in the display 11. Pressing control inputs 19 associated with, or adjacent to, an icon in the display may select a corresponding option that may change the operation of, for example, the monitor 12 and/or the sensor 10.

The sensor 10 may be a clip style sensor capable of being applied to, for example, a patient's finger. The sensor 10 may include an emitter 22 and a detector 24. As depicted, the emitter 22 and detector 24 may be arranged in a transmittance-type configuration in which the emitter 22 and detector 24 are typically placed on differing sides of the sensor site. In this manner, the detector 24 may detect light that has passed through one side of a tissue site to an opposite side of the tissue site. Alternatively, the sensor 10 may be a flexible bandage style sensor such as those available from Nellcor Puritan Bennett, LLC. This flexible bandage style sensor may be, for example, wrapped around a patient's finger and may be a reflectance style sensor in which the emitter 22 and detector 24 are placed on the same side of the sensor site. Reflectance type sensors may operate by emitting light into the tissue and detecting the reflected light that is transmitted and scattered by the tissue. That is, reflectance type sensors detect light photons that are scattered back to the detector 24.

Figure 2:
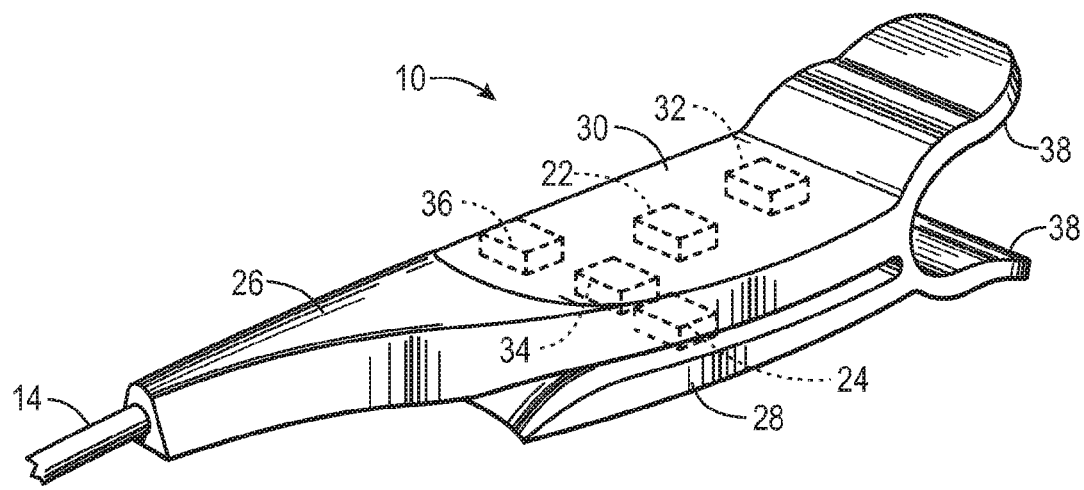
FIG. 2 is a perspective view of a clip style embodiment of the sensor assembly shown in FIG. 1, in accordance with an embodiment.

Turning now to FIG. 2, a perspective view of a clip-style embodiment of sensor 10 is shown. The sensor 10 includes an upper clip portion 26 and a lower clip portion 28. As depicted, upper clip portion 26 includes a housing 30, which houses the emitter 22, while the lower clip portion 28 may house the detector 24. In other embodiments the emitter 22 and detector 24 may be reversed. Additionally, the housing 30 may include one or more accelerometers 32, 34, and 36. In one embodiment, three accelerometers 32, 34, and 36 are utilized whereby each accelerometer 32, 34, and 36 measures acceleration in a particular direction in three dimensional space. In this manner, each accelerometer 32, 34, and 36 may measure specific directional acceleration of the sensor 10 so that the acceleration, and thus movement, of the sensor 10 may be measured so that the motion may be compensated for with respect to calculating the optical path between the emitter 22 and the detector 24. In this manner, signal attenuation between the emitter 22 and the detector 24 may be accounted for. Alternatively, a single tri-axis accelerometer may be utilized to measure all movements in three dimensional space for determination of motion for calculation of any changes in the optical path between the emitter 22 and the detector 24.

When three accelerometers 32, 34, and 36 are utilized, the accelerometers 32, 34, and 36 may be placed in the sensor 10, for example, orthogonally (i.e., at right angles to one another) in housing 30 or in the clip 38 of the sensor. For example, accelerometers 32, 34, and 36 may be placed in the upper clip portion 26, the lower clip portion 28, in the clip 38, or in some combination thereof (e.g., accelerometer 32 in the upper clip portion 26 and accelerometers 34 and 36 in the lower clip portion 28). Furthermore, each of the accelerometers 32, 34, and 36 may be a micro-electromechanical device capable of measuring movement in the sensor 10, i.e. acceleration relative to freefall. By measuring the movement of the sensor 10, potential effects from the motion of the sensor 10 may be adjusted when physiological parameters of a patient are calculated.

Figure 3:
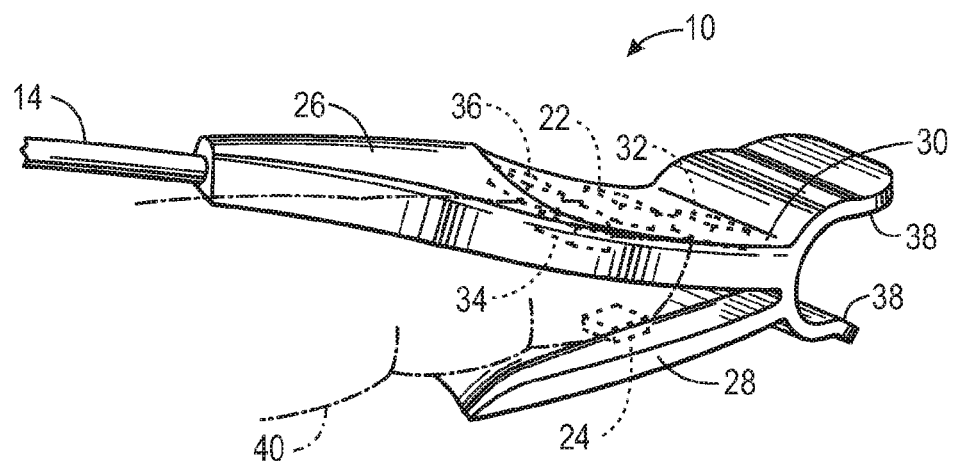
FIG. 3 is a perspective view of the sensor assembly shown in FIG. 2 placed on a patient's finger, in accordance with an embodiment.

FIG. 3 shows the clip-style embodiment of sensor 10 in operation. As depicted, upper clip portion 26 and lower clip portion 28 have been separated, allowing a patient's digit 40 to be inserted in the sensor 10. In one embodiment, light waves may be emitted by emitter 22 into the top of patient digit 40. The light waves may then be transmitted through the patient's digit 40 and received by detector 24. A signal corresponding to the detected light waves may be sent to the monitor 12 via cable 14. Additionally, any movements caused, for example, by tapping of the digit 40 or general movement of the digit 40 may be transmitted as movement signals from the accelerometers 32, 34, and 36 to the monitor 12 via the cable 14. As described below, these movement signals may be used to increase the reliability of calculated physiological characteristics of the patient.

Figure 4:
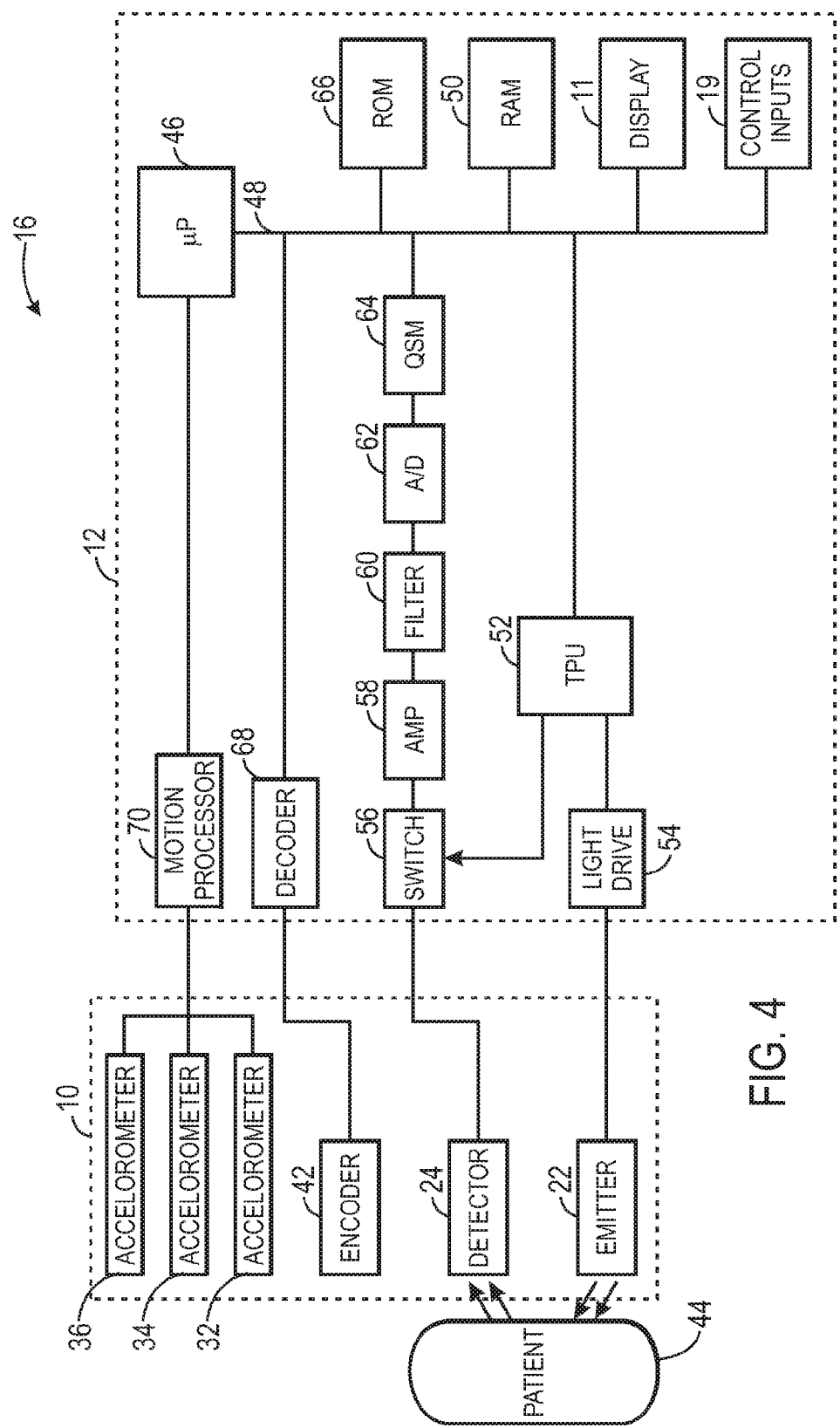
FIG. 4 illustrates a simplified block diagram of the pulse oximeter in FIG. 1, in accordance with an embodiment.

Turning to FIG. 4, a simplified block diagram of a pulse oximeter 16 is illustrated in accordance with an embodiment. Specifically, certain components of the sensor 10 and the monitor 12 are illustrated. As previously noted, the sensor 10 may include an emitter 22, a detector 24, and accelerometers 32, 34, and 36. The sensor 10 may also include an encoder 42. It should be noted that the emitter 22 may be capable of emitting at least two wavelengths of light, e.g., RED and infrared (IR) light, into the tissue of a patient 44 to calculate the patient's 44 physiological characteristics, where the RED wavelength may be between about 600 nanometers (nm) and about 700 nm, and the IR wavelength may be between about 800 nm and about 1000 nm. Alternative light sources may be used in other embodiments. For example, a single wide-spectrum light source may be used, and the detector 24 may be capable of detecting certain wavelengths of light. In another example, the detector 24 may detect a wide spectrum of wavelengths of light, and the monitor 12 may process only those wavelengths which are of interest for use in measuring, for example, water fractions, hematocrit, or other physiologic parameters of the patient 44. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

Additionally the sensor 10 may include an encoder 42, which may contain information about the sensor 10, such as what type of sensor 10 it is (e.g., whether the sensor 10 is intended for placement on a forehead or digit 40) and the wavelengths of light emitted by the emitter 22. Additionally and/or alternatively, the encoder may contain information about the accelerometers 32, 34, and 36. The information in the encoder 42 may allow the monitor 12 to select appropriate algorithms and/or calibration coefficients for calculating the patient's 44 physiological characteristics. Additionally, the encoder 42 may include information relating to the proper charging of the sensor 10. The encoder 42 may, for instance, be a memory on which one or more of the following information may be stored for communication to the monitor 12; the type of the sensor 10; the wavelengths of light emitted by the emitter 22; and the proper calibration coefficients and/or algorithms to be used for calculating the patient's 44 physiological characteristics. The sensor 10 may be any suitable physiological sensor, such as those available from Nellcor Puritan Bennett LLC.

As previously described, the signals used in conjunction with the emitter 22 and the detector 24 may be utilized for the monitoring of physiologic parameters of the patient 44 while the signals from the encoder 42 may contain information about the sensor 10 to allow the monitor 12 to select appropriate algorithms and/or calibration coefficients for calculating the patient's 44 physiological characteristics. To aid in this calculation, the monitor 12 may further include one or more processors 46 coupled to an internal bus 48. Also connected to the bus 48 may be a RAM memory 50 and the display 11. A time processing unit (TPU) 52 may provide timing control signals to light drive circuitry 54, which controls when the emitter 22 is activated, and if multiple light sources are used, the multiplexed timing for the different light sources. TPU 52 may also control the gating-in of signals from detector 24 through a switching circuit 56. The TPU 52 may control the gating-in of signals from detector 24 to insure that the signals are sampled at the proper time, which may depend at least in part upon which of multiple light sources is activated, if multiple light sources are used. The received signal from the detector 24 may be passed through an (optional) amplifier 58, a low pass filter 60, and an analog-to-digital converter 62 for amplifying, filtering, and digitizing the electrical signals the from the sensor 10. The digital data may then be stored in a queued serial module (QSM) 64, for later downloading to RAM 50 as QSM 64 fills up. In an embodiment, there may be multiple parallel paths of separate amplifier, filter, and A/D converters for multiple light wavelengths or spectra received.

In an embodiment, based at least in part upon the received signals corresponding to the light received by detector 24, processor 46 may calculate the oxygen saturation using various algorithms. These algorithms may use coefficients, which may be empirically determined, and may correspond to the wavelengths of light used. The algorithms may be stored in a ROM 66 and accessed and operated according to processor 46 instructions. The monitor 12 may also include a decoder 68 that may receive signals from the encoder 42. The decoder 68 may, for instance, decode the signals from the encoder 42 and may provide the decoded information to the processor 46. The decoded signals may provide information to the processor 46 such as the type of the sensor 10 and the wavelengths of light emitted by the emitter 22 so that proper calibration coefficients and/or algorithms to be used for calculating the patient's 44 physiological characteristics may be selected and utilized by the processor 46.

As may be seen in FIG. 4, the monitor 12 may also include a motion processor 70. The motion processor 70 may include one or more microprocessors, such as one or more "general-purpose" microprocessors, one or more special-purpose microprocessors and/or application specific integrated circuits (ASICS), or some combination of such processing components. The motion processor 70 may be a part of the processor 46, or the motion processor 70 may be distinct from processor 46. Motion processor 70 may be coupled to accelerometers 32, 34, and 36 and may receive signals from the accelerometers 32, 34, and 36. These signals may correspond to motion in three dimensional space of the sensor 10. For example, the three dimensional space may be represented by a Cartesian coordinate system that may be represented as points relative to three axes (e.g., x, y, and z), where each of the axes may be perpendicular to the other two at the point at which they cross (e.g., at their origin). Accordingly, the accelerometer 32 may transmit a signal corresponding to motion in an x direction; accelerometer 34 may transmit a signal corresponding to motion in a y direction; and accelerometer 36 may transmit a signal corresponding to motion in a z direction, where the x, y, and z directions are orthogonal to one another and represent three dimensional Cartesian space as described above. Alternatively, a single tri-axis accelerometer, for example, placed along the axis of the emitter 22 and the detector 24, may be utilized to measure all movements in three dimensional space for determination of motion for calculation of any changes in the optical path between the emitter 22 and the detector 24. The motion processor 70 may receive signals from each of the accelerometers 32, 34, and 36 or the single tri-axis accelerometer and may calculate an attenuation factor that accounts for the effect of the detected motion (e.g., acceleration), for example, on the optical signal path between the emitter 22 and the detector 24, as described below with respect to FIG. 5.

Figure 5:
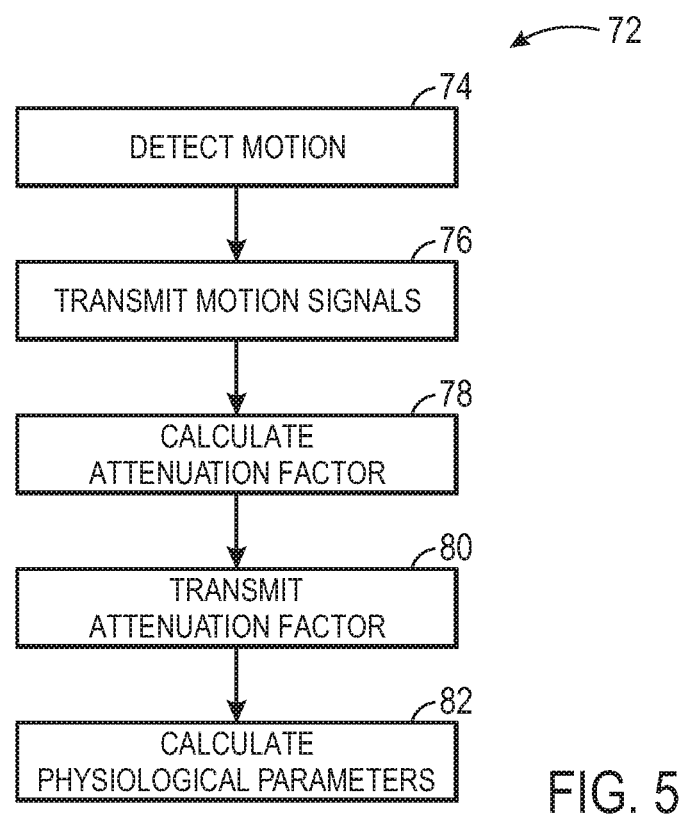
FIG. 5 illustrates a flow chart of the operation of a pulse oximeter in FIG. 1, according to an embodiment.

FIG. 5 illustrates a flowchart 72 that details an example of a procedure for detecting motion in the sensor 10 as well as accounting for the effects of the detected motion. In step 74, the accelerometers 32, 34, and 36 may detect motion in the sensor 10. This motion may be generated through physical movement of the sensor 10, such as moving a digit 40 surrounded by the sensor 10, or through a combination of compression and/or movement of the sensor 10, such as generated by a patient 44 tapping a digit 40 covered with the sensor 10 on a surface. Movement and/or compression of the sensor 10 may cause signal interference, such that signal artifacts are generated during movement, which may dwarf or mask the pulsatile waveform. Because the monitor 12 is typically calibrated to determine physiological parameters of the patient 44 based on a fixed distance between the emitter 22 and the detector 24, change in the distance therebetween may adversely affect the calculated results. Furthermore, any change in the relative positions of the emitter 22 and detector 24 on the tissue bed of the patient 44 may generate signal interference that can easily mask the underlying pulsatile waveform. For example, the monitor 12 may be calibrated to calculate physiological parameters of the patient 44 based on light traveling a distance d from the emitter 22 to the detector 24. Compression of the tissue may cause the distance d to be lessened, thus potentially causing changes in the amount and strength of the light detected at the detector 24. Additionally, compression of the tissue may cause the photons passing from the emitter 22 to the detector 24 to behave in a different manner, i.e., the tissue compression may cause the tissue to be more dense than decompressed tissue, causing a higher rate of absorption of the photons transmitted between the emitter 22 and the detector 24. Accordingly, absent any indicia that the tissue or the distance between the emitter 22 and the detector 24 has been modified, the monitor 12 will calculate physiological parameters based on the received light at a distance d instead of at the actual distance (e.g., less than or greater than d).

In another example, movement of a patient may generate an air gap between the site of a patient 44 being monitored (e.g., a digit 40) and either the emitter 22 or the detector 24.

This air gap can transmit the light substantially differently than light transmitted through tissue of the digit 40. Accordingly, absent any indicia that the movement of the sensor 12 is of the type to induce an air gap, the monitor 12 will calculate physiological parameters based on the received light as if the light has not passed through an air gap.

To overcome these potential calculation errors, the accelerometers 32, 34, and 36 may measure movement of the sensor 10, the emitter 22, and/or the detector 24. This measurement may be transmitted from the accelerometers 32, 34, and 36 in step 76. As such, any of the accelerometers 32, 34, and 36 registering movement may transmit the measurements to the monitor 12 (specifically to the motion processor 70) via, for example, cable 14. The motion processor 70 may receive these measurements and may calculate an attenuation factor based on the received measurements in step 78.

The calculation of an attenuation factor in step 78 may be based on the received measurements transmitted in step 76. As described above, the measurements may be based on movement (e.g., acceleration) of the sensor 10 that may cause the optical signal path between the emitter 22 and the detector 24 to change. The measurements motion processor may calculate an attenuation factor that will compensate for the motion of the sensor 10. This calculation may be made utilizing, for example, an equation that takes into account the model optical distance between the emitter 22 and the detector 24, an expectation model of photon behavior in the patient's 44 tissue, and the received measurements. The equation for the reflectance of a turbid media such as tissue may be given by the following relation:

$$R(\rho, \mu_a, \mu_s') = C_1\Phi(\rho) + C_2 J_z(\rho)$$

where C1 and C2 are constants relating to the coupling parameters of fiber to tissue, and $\Phi(\rho)$ and $J_z(\rho)$ are given by:

$$\Phi(\rho) = \frac{1}{4\pi D}\left(\frac{\exp(-\mu_{eff} r_1(\rho))}{r_1(\rho)} - \frac{\exp(-\mu_{eff} r_2(\rho))}{r_2(\rho)}\right)$$

and $$J_z(\rho) = \frac{1}{4\pi\mu_t}\left(\left(\mu_{eff} + \frac{1}{r_1(\rho)}\right)\frac{\exp(-\mu_{eff} r_1(\rho))}{r_1^2(\rho)} + \left(2z_b + \frac{1}{\mu_t}\right)\left(\mu_{eff} + \frac{1}{r_2(\rho)}\right)\frac{\exp(-\mu_{eff} r_2(\rho))}{r_2^2(\rho)}\right)$$

Where $$D = \frac{c}{3(\mu_s' + \mu_a)}$$

$$\mu_t = \mu_a + \mu_s'$$

$$\mu_{eff} = \sqrt{3\mu_a \mu_t}$$

Accordingly, the reduced scattering and absorption coefficients become functions of the acceleration vector defined by the spectrometer since various accelerations may produce changes related to physiologic parameters such as "venous sloshing", tissue compression, arterial pressure changes, etc. The change in position of the emitter 22 and detector ($\rho$) 24 will be adjusted directly from the position changes from one or more of the accelerometers 32, 34, and 36.

These elements may be combined to calculate and generate the attenuation factor, which may relate to the amount that signals from the emitter 22 to the detector 24 are attenuated (i.e., the attenuation factor may relate to photon behavior in the tissue of the patient 44, tissue compression/decompression, and/or any air gaps between the tissue and the emitter 22 and/or the detector 24).

In another embodiment, the calculation of the attenuation factor (step 78) may be made utilizing look-up tables or other stored data results. For example, the received measurements (e.g., motion signals) may be compared to a set of programmed measurements values (e.g., attenuation factors) and the most similar programmed measurement value to the received measurement may be selected. Based on this selection, the motion processor 70 may read out an attenuation factor corresponding to the selected programmed measurement. These attenuation factors may be determined based on an equation that takes into account the model optical distance between the emitter 22 and the detector 24, an expectation model of photon behavior in the patient's 44 tissue, and the received measurements. These elements may be combined to calculate and generate the attenuation factor, which may relate to the amount that signals from the emitter 22 to the detector 24 are attenuated (i.e., the attenuation factor may relate to photon behavior in the tissue of the patient 44, tissue compression/decompression, and/or any air gaps between the tissue and the emitter 22 and/or the detector 24). The process of reading out attenuation factors corresponding to the selected programmed measurements may be repeated for any measurements received from accelerometers 32, 34, and 36. That is, if more than one measurement is received (i.e., if more than one of the accelerometers 32, 34, and 36 measures movement) the motion processor 70 may combine (or keep separate) the attenuation factors corresponding to the received measurements. The determined attenuation factors may be transmitted to the processor 46 in step 80.

The processor 46 may receive the attenuation factor from the motion processor 70 in step 82. Based on the received attenuation factor, the processor 46 may make adjustments to the calculation of the physiological parameters of the patient 44. For example, the attenuation factor may be used to change the value of a pulse that corresponds to a physiological parameter of a patient 44 at a given time. The attenuation factor may be applied in a calculation by the processor 46 to remove any effects of motion on the calculated physiological parameter. For example, the attenuation factor may alter the algorithms selected by the processor 46 for use in calculating various physiological parameters of the patient 44. As previously noted, based at least in part upon the received signals corresponding to the light received by detector 24, processor 46 may calculate the oxygen saturation using various algorithms. These algorithms may use coefficients, which may be empirically determined, and may correspond to the wavelengths of light used. The algorithms may be stored in a ROM 66 and accessed and operated according to processor 46 instructions. The attenuation factors may provide the processor 46 with information related to the actual distance between the emitter 22 and the detector 24, the photon behavior in either compressed or decompressed tissue, and/or any air gaps so that the processor 46 may select proper calibration coefficients and/or algorithms to be used for calculating the patient's 44 physiological characteristics by the processor 46.

Furthermore, pulse identification and qualification may be boosted through selection of the proper coefficients via incorporating the attenuation factors in the selection process. As described above, digitized optical signals may be provided to the processor 46 and proper coefficients for calculating the patient's 44 physiological characteristics may be selected based on these digitized optical signals. However, before the physiological characteristics are calculated, pulses in the digitized optical signals may first be identified and qualified as likely arterial pulses. This may be performed by the processor 46 utilizing a pre-trained neural network. Furthermore, the attenuation factors may be utilized by the processor 46 as, for example, an input to the neural network or a selection criterion for results of the neural network. In this manner, the processor 46 may identify the pulses by examining their amplitude, shape, and frequency, specifically pre-processed red and infra-red signals, average pulse period, lowpass waveforms from the low pass filter 60 and the results may include indications of the degree of arrhythmia, pulse amplitude variations, individual pulse quality, pulse beep notification, and qualified pulse periods and age, (i.e. the outputs may indicate the degree of arrhythmia and individual pulse quality). Through the use of the attenuation factors, a greater number of qualified pulses may be generated. Further, based on the greater number of qualified (i.e. reliable) pulses, the veracity of the measurements displayed on the display 11, and, thus, the overall reliability of the pulse oximeter 16 may be increased.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims.

What is claimed is:

1. A physiological sensor comprising:
an emitter configured to transmit light;
a detector configured to receive the transmitted light;
a first accelerometer disposed on a first portion of the sensor; and
a second accelerometer disposed on a second portion of the sensor, wherein the second portion opposes the first portion, and the first and second accelerometers are configured to measure a change in motion that corresponds to a change in distance between the detector and the emitter.

2. The physiological sensor, as set forth in claim 1, comprising a third accelerometer configured to be disposed on the first portion or the second portion.

3. The physiological sensor, as set forth in claim 2, wherein the first accelerometer is configured to generate a first signal corresponding to the change in distance in a first direction between the detector and the emitter, the second accelerometer is configured to generate a second signal corresponding to the change in distance in a second direction between the detector and the emitter, and the third accelerometer is configured to generate a third signal corresponding the change in distance in a third direction between the detector and the emitter.

4. The physiological sensor, as set forth in claim 2, wherein the first accelerometer, the second accelerometer, and the third accelerometer are orthogonally located with respect to one another.

5. The physiological sensor, as set forth in claim 1, wherein the sensor comprises a clip style sensor configured to clip to a tissue of a patient.

6. The physiological sensor, as set forth in claim 1, comprising an encoder comprising information related to the sensor's characteristics.

7. The physiological sensor, as set forth in claim 1, comprising an encoder comprising information related to the first and second accelerometers.

8. The physiological sensor, as set forth in claim 1, wherein the emitter and the detector are disposed in the first portion of the sensor.

9. The physiological sensor, as set forth in claim 1, wherein the sensor is coupled to a transmitter configured to facilitate wireless communication between the sensor and a monitor.

10. A physiological sensor comprising:
a clip style sensor body comprising:
a first portion comprising an emitter configured to transmit light and a first accelerometer;
a second portion opposing the first portion, the second portion comprising a second accelerometer, wherein the first and second accelerometers are configured to detect a change in motion.

11. The physiological sensor, as set forth in claim 10, wherein the second portion comprises a detector configured to receive light transmitted by the emitter after the light passes through a patient's tissue.

12. The physiological sensor, as set forth in claim 10, comprising a third accelerometer configured to be disposed in the first portion or the second portion.

13. The physiological sensor, as set forth in claim 12, wherein the first accelerometer is configured to generate a first signal corresponding the change in distance in a first direction between the detector and the emitter, the second accelerometer is configured to generate a second signal corresponding to the change in distance in a second direction between the detector and the emitter, and the third accelerometer is configured to generate a third signal corresponding the change in distance in a third direction between the detector and the emitter.

14. The physiological sensor, as set forth in claim 10, comprising an encoder comprising information related to the sensor's characteristics.

15. The physiological sensor, as set forth in claim 10, comprising an encoder comprising information related to the first and second accelerometers.

16. A pulse oximetry system comprising:
a sensor comprising:
a first portion comprising an emitter configured to transmit light and a first accelerometer;
a second portion opposing the first portion and comprising a detector configured to receive the light and a second accelerometer, wherein the first and second portions are configured to be clipped to a tissue of a patient, and wherein the first and second accelerometers are configured to detect a change in motion; and
a pulse oximetry monitor configured to be coupled to the sensor, wherein the pulse oximetry monitor comprises a motion processor configured to receive signals from the first and second accelerometers related to the change in motion detected by the first and second accelerometers and to determine a change in distance between the detector and the emitter based on the received signals.

17. The pulse oximetry system, as set forth in claim 16, wherein the motion processor is configured to calculate an attenuation factor that accounts for the effect of the detected motion.

18. The pulse oximetry system, as set forth in claim 16, wherein the pulse oximetry monitor is configured to utilize the change in motion detected by the first and second accelerometers to calculate a physiological parameter.

19. The pulse oximetry system, as set forth in claim 16, comprising a display configured to display a representation of the physiological parameter.

* * * * *